United States Patent [19]

Skolnick et al.

[11] Patent Number: 6,017,957
[45] Date of Patent: Jan. 25, 2000

[54] PARTIAL AGONISTS OF THE STRYCHNINE INSENSITIVE GLYCINE MODULATORY SITE OF THE N-METHYL-D-ASPARTATE RECEPTOR COMPLEX AS NEUROPSYCHOPHARMACOLOGICAL AGENTS

[75] Inventors: Phil Skolnick, Potomac, Md.; Anita Lewin, Chapel Hill, N.C.; Juan-Carlos Marvizon, Madrid, Spain; James Monn, Gaithersburg; Kenner Rice, Bethesda, both of Md.

[73] Assignee: The United States of America as represented by the Department of Health and Human Services, Washington, D.C.

[21] Appl. No.: 07/390,745

[22] Filed: Aug. 8, 1989

[51] Int. Cl.$^7$ .................................................. A61K 31/215
[52] U.S. Cl. ........................... 514/531; 514/561; 560/124
[58] Field of Search ............................ 560/124; 514/531, 514/561

[56] References Cited

U.S. PATENT DOCUMENTS

| | | | |
|---|---|---|---|
| 4,491,589 | 1/1985 | Dell et al. ................................ | 514/400 |
| 4,554,017 | 11/1985 | Schroder et al. ......................... | 71/113 |
| 4,746,653 | 5/1988 | Hutchison et al. . | |
| 5,086,072 | 2/1992 | Trullus et al. ........................... | 514/501 |

OTHER PUBLICATIONS

Bonta et al, Brit. J. Pharmacol. 43(3) 514–35, 1971.
Singh et al Proc. Natl. Acad. Sci. USA 87, 347–351, 1990.
Nadler et al, European Journal of Pharmacology, vol. 157, pp. 115–116, 1988.
Marvizón et al, J Neurochem, vol. 52, p. 992–994, 1989.
Robinson et al, FASEB J, vol. 1, pp. 446–455, 1987.
Faster et al, Nature, vol. 392, pp. 395–396, 1987.
P. Skolnick et al, Life Sciences, vol. 45, No. 18 (1989), pp. 1647–1655.
R. Trullas et al, Pharm.Bioch. & Beh., vol. 34, (1989), pp. 313–316.
D. W. Choi, Neuron, vol. 1, Oct. 1988, pp. 623–934.
J. T. Winslow et al, Europ. J. of Pharm., vol. 190 (1990), pp. 11–21.
J. D. Leander et al, Brain Research, vol. 448 (1988), pp. 115–120.
J. Lehman et al, Drug Discov. Div., Ciba–Geigy Corp., pp. 31–40.
C. Cotman et al, J. of NIH Res., vol. 1, pp. 65–74 (1989).
J. W. Olney, Biol. Psychiatry, vol. 26, (1989), pp. 505–525.

*Primary Examiner*—Gary Geist
*Attorney, Agent, or Firm*—Arnall Golden & Gregory, LLP

[57] ABSTRACT

A method is disclosed for the treatment of neuropsychopharmacological disorders which are associated with or result from excessive activation of the N-methyl-D-aspartate receptor complex, which method comprises administering an effective neuropsychopharmacological disorder-treating amount of a compound possessing partial agonist properties for the strychnine insensitive glycine modulatory sites of N-methyl-D-aspartate receptors. Exemplary of partial agonists which are useful in the method of the invention are 1-aminocyclopropanecarboxylic acid, and associated derivates thereof. Novel injectable pharmaceutical compositions are also disclosed.

21 Claims, No Drawings

PARTIAL AGONISTS OF THE STRYCHNINE INSENSITIVE GLYCINE MODULATORY SITE OF THE N-METHYL-D-ASPARTATE RECEPTOR COMPLEX AS NEUROPSYCHOPHARMACOLOGICAL AGENTS

BACKGROUND OF THE INVENTION

The N-methyl-D-aspartate (NMDA) subtype of glutamate receptor and its associated cation channel are allosterically coupled to a strychnine-insensitive glycine receptor, forming a "supramolecular complex" (reviewed in Foster and Fagg, 1987). Excessive activation of this "supramolecular complex" has been linked to various neuropsychopharmacological disorders including seizure disorders, ischemic brain damage, and other neuropathologies (Lehmann et al, 1987; Robinson and Coyle, 1987). The structural requirements for ligand binding to strychnine-insensitive glycine receptors in this "supramolecular complex" (Kishimoto et al, 1981; Marvizón et al, 1986; Galli et al, 1988; Snell et al, 1988) and their regional distribution in the central nervous system (Bristow et al, 1986) have been reported to differ remarkably from strychnine-sensitive glycine receptors. It has also been reported that there is an absolute requirement that there be present glycine for activation of NMDA receptor complexes as expressed in Xenopus oocytes (Kleckner and Dingledine, 1988).

1-Aminocyclopropanecarboxylic Acid (ACPC) has been shown to be potent and selective partial agonist of the strychnine insensitive glycine binding site of the N-methyl-D-aspartate (NMDA) receptor complex (Marvizón, 1989).

SUMMARY OF THE INVENTION

The present invention provides for:

1. A method for treating a neuropsychopharmacological disorder in a patient, wherein the neuropsychopharmacological disorder treated is associated with or resulting from excessive activation of the N-methyl-aspartate receptor complex, said method comprising: administering to said patient possessing a neuropsychopharmacological disorder an effective amount of a compound which possesses partial agonist properties for the strychnine insensitive glycine modulatory site of the N-methyl-D-aspartate receptor complex.

2. The method of paragraph (1), wherein the neuropsychopharmacological disorder treated is selected from:
epilepsy, stroke, anxiety, Alzheimer's disease, Parkinson Disease, Guam ALS, dementia, and lathyrism.

3. The method of paragraphs (1) and (2), wherein compound possessing partial agonist properties for the strychnine insensitive glycine modulatory site of the N-methyl-D-aspartate receptor complex and used to treat said neuropsychopharmacological disorders is a compound having the formula:

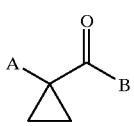

Formula I wherein
A is —NH$_2$, —NHR$^1$ or —NR$^1$R$^2$;
B is —OH or —OR$^3$;
R$^1$, R$^2$ and R$^3$, same or different, are selected from lower alkyl, which may be substituted by halogen, hydroxyl, alkoxy, oxo, mercapto, aryl or amino; or a pharmaceutically acceptable salt thereof.

4. The method of paragraphs (1) and (2), wherein said compound possessing partial agonist properties for the strychnine insensitive glycine modulatory site of the N-methyl-D-aspartate receptor complex, and used to treat said neuropsychopharmacological disorders, is a compound having the formula:

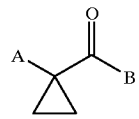

Formula Ia wherein
A$^1$ is —NH$_2$, —NHR$^1$ or —NR$^1$R$^2$;
B$^1$ is —OH or —OR$^3$;
R$^1$, R$^2$ and R$^3$, same or different are lower alkyl, or a pharmaceutically acceptable salt thereof.

5. The method of paragraphs (1) and (2), wherein said compound possessing partial agonist properties for the strychnine insensitive glycine modulatory site of the N-methyl-D-aspartate receptor complex and used to treat said neuropsychopharmacological disorders is:
1-aminocyclopropanecarboxylic acid,
1-aminocyclopropanecarboxylic acid methyl ester,
1-aminocyclopropanecarboxylic acid ethyl ester; or
a pharmacologically acceptable salt thereof.

6. The method of paragraphs (4) and (5), wherein said neuropsychopharmacological disorder is an epilepsy or anxiety disorder.

7. A sterile injectable pharmaceutical composition comprising an effective neuropsychopharmacological disorder-treating amount of a compound having the formula:

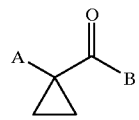

Formula I wherein
A is —NH$_2$, —NHR$^1$ or —NR$^1$R$^2$;
B is —OH or —OR$^3$;
R$^1$, R$^2$ and R$^3$, same or different, are selected from lower alkyl, which may be substituted by halogen, hydroxyl, lower alkoxy, oxo, thiol, aryl or amino; or a pharmaceutically acceptable salt thereof; and (b) a pharmaceutically acceptable carrier therefor.

8. A sterile pharmacological composition for administration by injection said composition comprising an effective neuropsychopharmacological disorder treating amount of:
1-aminocyclopropanecarboxylic acid,
1-aminocyclopropanecarboxylic acid methyl ester, or
1-aminocyclopropanecarboxylic acid ethyl ester; and
a pharmaceutically acceptable carrier therefor.

The following is a glossary of terms utilized herein, the same is provided to remove any vagueness, which may exist as to the meaning of such terms.

The term "partial agonist" as used herein means having partial agonist properties when compared with the endogenous neurotransmitter glycine.

The term "neuropsychopharmacological disorder" as utilized herein, unless otherwise qualified, means a disorder resulting from or associated with excess activation of the N-methyl-D-aspartate receptor complex, and a possible glutamate neurotoxicity resulting therefrom. Such disorders may be the result of acute brain injury, or may be the result of chronic neuronal degeneration. More specifically, the following neuropsychopharmacological disorders are included within the definition: epilepsy (or seizures), hypoxia, either alone (e.g., carbon monoxide poisoning, near drowning) or combined with ischemic blood flow reduction (e.g., cardiac arrest, stroke); anxiety, and neurodegenerative diseases (e.g., Guam ALS, Parkinson disease, Alzheimer disease, dementia and lathyrism) which are associated with or result from excessive activation of the N-methyl-D-aspartate receptor complex, and glutamate neurotoxicity resulting therefrom.

The term "lower alkyl" as used herein, means an alkyl radical having 1–9 carbon atoms, which may be straight or branched, including, for example, methyl, ethyl, propyl, isopropyl, butyl, isobutyl, tertbutyl, amyl, isoamyl, hexyl, heptyl, octyl, nonyl, or the like.

The term "halogen" as used herein refers to fluorine, chlorine, bromine, and iodine atoms.

The term "hydroxyl" as used herein means —OH.

The term "lower alkoxy" as used herein means lower alkyl—O—.

The term "oxo" as used herein means an =O group.

The term "mercapto" as used herein means a —SH group.

The term "aryl" as used herein means an organic radical derived from an aromatic hydrocarbon, e.g., phenyl from benzene.

The term "amino" as used herein means $—NH_2$.

The term "pharmaceutically acceptable salt" as used herein includes acid addition salts, hydrates, alcolates and salts of Formula I compounds disclosed herein which are psysiologically compatible in warm blooded animals. The acid addition salts may be formed by either strong or weak acids. Representative of strong acids are hydro-chloric, sulfuric and phosphoric. Representative of weak acids are fumaric maleic, succinic, oxalic, citric, tartaric, cyclohexaminic and the like.

The term "amino protecting group" as used herein, in synthesis methods means an acyl or benzoyl radical, or the like.

The following list of abbreviations utilized herein is also provided to remove any vagueness which may exist to their meanings.

1-aminocyclopropanecarboxylic acid, ACPC; methyl 1-aminocyclopropanecarboxylate, ACPCM; ethyl 1-aminocyclopropanecarboxylate, ACPCE; N-methyl-D-aspartate, NMDA; (+)-5-Methyl-10,11-dihydro-5H-dibenzo [a,d]cyclo-hepten-5,10-imine, MK-801; thienycyclohexylpiperidine, TCP; pentylenetetrazol, PTZ; bicuculline, bicuc.; strychnine hemisulfate, strych.; maximal electroshock seizures, MES.

DETAILED DESCRIPTION OF THE INVENTION

The present invention is concerned with treating neuropsychopharmacological disorders associated with excessive activation of the N-methyl-D-aspartate receptor complex. More specifically, it is concerned with utilizing partial agonist of the strychnine insensitive glycine receptor (which is allosterically coupled to the NMDA receptor complex to form a supramolecular complex) to control such neuropsychopharmacological disorders. By utilizing such partial agonist of the strychnine insensitive glycine receptor, (such partial agonist being herein exemplified by 1-aminocarboxylic acid and associated derivatives thereof which are encompassed by Formula I), one may with the method of the present invention treat neuropsychopharmacological disorders, associated with or resulting from excessive activation of the NMDA receptor complex. Furthermore, by utilizing partial agonist, as taught herein, one may treat neuropsychopharmacological disorders without producing possible unwanted side effects which can occur when blockage of the NMDA receptor complex is maintained, by administering either competitive or noncompetitive antagonist of the NMDA receptor. Exemplary of possible side effects avoided by utilizing our herein disclosed partial agonists (versus antagonists of the NMDA receptor), would include, for example, schizophrenia-like symptoms in patients, loss of normal NMDA receptor-mediated synaptic plasticity (which can possibly affect learning and memory in a patient), amnesia, confusional states and muscle relaxation.

Moreover, we show below, in the provided Experimental Section, that 1-ACPC, a partial agonist of the strychnine insensitive glycine receptor possessed a greater therapeutic index than competitive or non-competitive antagonists of the NMDA receptor. The same making applicants' disclosed method for treating neuropsychopharmacological disorders with partial agonists, unexpected beneficial, inasmuch as partial agonists of the strychnine insensitive glycine receptor can be utilized by one skilled in the art to elicit a desired therapeutic result, without worry of producing certain neurotoxic side effects.

Compounds of Formula I which are useful in the methods of the present invention and can be commercially purchased or can generally be prepared by methods readily known and understood by those skilled in the art. For example, lower alkyl esters of 1-aminocyclopropanecarboxylic acid can be prepared by Fischer esterification of the parent compound. Additionally, for example, compounds wherein "A" is a lower alkylamino or lower dialkylamino moiety can be easily prepared by reacting 1-aminocyclopropanecarboxylic acid lower alkyl esters with designed lower alkyl halides, while protecting sites on the amino moiety with "amino protection groups" when needed, and deprotecting thereafter by usual means.

In order to more fully disclose the present invention, the following Experimental Section is included to exemplify both the effectiveness and selectivity associated with administering partial agonists of the strychnine insensitive glycine receptor site, to treat neuropsychopharmacological disorders associated with excessive activation of the NMDA receptor complex. While in the experimental section which follows, compounds which are tested are limited to 1-aminocyclopropanecarboxylic acids and esters thereof, this is in no way to be construed as limiting to applicants' general disclosure herein of treating neuropsychological disorders with partial agonists of the strychnine in sensitive glycine receptor site, or to diminish the scope of protection afforded the inventors hereof by disclosure of the same.

The following Experimental Section is divided into sections relating to materials and methods utilized, results obtained, and a discussion of results. Following the Experimental Section, there are provided suitable pharmaceutical formulations for administering by injection those partial agonists of strychnine insensitive glycine receptors which are encompassed by Formula I, provided herein.

EXPERIMENTAL SECTION MATERIALS AND METHODS

Evaluation of anticonvulsant activity

Male (25–30 g) NIH-Swiss mice (Harlan Sprague-Dawley, Frederick, Md.) were group housed in 32 cm×25 cm×15 cm plastic cages (10–15/cage) with food and water freely available. Mice were injected intraperitoneally with the test substance and challenged fifteen minutes later (unless otherwise specified) with NMDA (125 mg/kg), pentylenetetrazole (PTZ) (80mg/kg), strychnine (strych.) hemisulfate (2 mg/kg, as the base), bicuculline (bicuc.) (6 mg/kg) or maximal electroshock (MES). NMDA, PTZ, and strych. hemisulfate were dissolved in distilled water. Bicuculline was dissolved in 0.01 N HC1. These compounds were injected in a volume of 0.1 ml 1-aminocyclopropanecarboxylates were dissolved in distilled water and doses $\leq 500$ mg/kg injected in a volume of 0.1 ml; doses >500 mg/kg were injected in proportionately larger volumes. Immediately after convulsant challenge, mice were placed in 28.5 cm×17.8 cm×12 cm plastic cages (1/cage) and observed for 15 minutes. The presence or absence of convulsions and the time to the first convulsive episode (latency) were noted. MES were produced by applying a 50 mA current through alligator clips attached to the pinnae for 0.2 s.

Evaluation of motor performance:

Motor performance was evaluated using a rotarod apparatus (Dunham and Miya, 1956) and a modification of the horizontal wire test (Hunkeler et al, 1981). Mice were pretested on the rotarod (Rotamex meco, Columbus Instruments, Columbus, Ohio) prior to drug treatment as previously described (Marwaha et al, 1981). In the horizontal wire test, mice were injected with test compound and placed ten minutes later on a 25 cm wire (2 mm diameter) suspended 45 cm above a laboratory bench. The ability of a mouse to remain on the wire was monitored for two minutes. Animals were then transferred to the rotarod and evaluated at a speed of 5 rpm for 3 minutes. In some experiments, animals evaluated for motor performance were then administered MES.

Evaluation of 1-aminocyclopropanecarboxylates as inhibitors of [$^3$H] glycine binding Membrane preparation: Synaptic membranes were prepared from forebrains of adult (250–350 g) male Sprague-Dawley rats (Taconic Farms, Germantown, N.Y.) by modification of the method of Bristow et al, (1986). In brief, forebrains (whole brain minus cerebellum and brainstem) were weighed and then disrupted for 30 s (Ultra-Turrax, Model STD) in 10 volumes of 0.32 M sucrose containing 5 mM HEPES/4.5 mM Tris pH 7.4. The homogenate was diluted to 50 volumes with this buffer and centrifuged for 10 minutes (1000×g). The supernatant was decanted and centrifuged 20 minutes at 23000×g, the resulting pellet was resuspended in 50 volumes of HEPES-Tris buffer (5 mM HEPES/4.5 mM Tris, pH 7.4) and this centrifuged 20 minutes at 8000×g. The supernatant plus the upper, buffy coat of the pellet were collected and centrifuged at 23000×g. The pellet was then resuspended in 50 volumes of HEPES-Tris buffer and recentrifuged. This latter "washing" step was repeated four times. In the first two of these washes, 1 mM EDTA was included in the HEPES-Tris buffer to eliminate divalent cations. The pellet obtained after the fourth washing step was resuspended in 5 volumes of HEPES-Tris buffer, frozen in dry ice and stored (3 ml aliqots) at $-80°$ C. until used.

[$^3$H]Glycine binding: Immediately prior to assay, aliquots were thawed at 0–40 and "washed" 3 more times as described above. Membranes (0.1–0.3 mg prot.) were incubated for 60 minutes at 0–4° in HEPES-Tris buffer containing 1 mM MgCl$_2$, ([$^3$H]glycine (20 Ci/mmol, ISN, Irvine, Calif.), and drugs as indicated. Nonspecific binding was defined using 1 mM glycine. Incubations (1 ml) were terminated by centrifugation (Eppendorf Model 5414 Microfuge, 5 minutes) and the pellets washed superficially with 1 ml of assay buffer. The pellets were solubilized with 0.5 ml of NCS (Amersham, Arlington Heights, Ill.), agitated for 45 minutes, and 0.05 ml of glacial acetic acid added. Four ml of OCS (Amersham) was added and the radioactivity measured in a Beckman LS 5801 liquid scintillation counter.

Preparation of methyl-(ACPCM) and ethyl-(ACPCE) 1-aminocyclopropanecarboxylates and (+) −MK-801:

The methyl- and ethyl-esters of ACPC were prepared as the HCl salts by Fischer esterification of the parent compound with the appropriate alcohol and anhydrous HCl gas (Tsang et al, 1984). Spectral (IR, $^1$H-NMR) and analytical (melting point, CHN analysis) properties of these compounds were fully consistent with those previously reported (Tsang et al, 1984; Silverman et al, 1986). Racemic 5-methyl-10-,11-dihydro-5H-dibenzocylo hepten[a,d]imine was prepared by the method of Lamanec et al, (1988). Optical resolution was achieved by fractional crystallization of the diasteriomeric di-0,O'-p-toluoyl-D-tartaric acid salts (Anderson et al, 1982). The resulting (+)- isomer, MK-801, was converted to the monooxalate salt for use in vivo.

Materials

ACPC and pentylenetetrazole (PTZ) were purchased from Fluka (Ronkonkama, NY) and ICN/K K Laboratories (Plainview, N.Y.), respectively. Strychnine (Strych.) hemisulfate, glycine, bicuculline (bicuc.), and NMDA were obtained from Sigma Chemical Co., St. Louis, Mo. All other materials were obtained from standard commercial sources.

Results Effects of 1-aminocyclopropanecarboxylates on chemically-induced convulsions:

NMDA (125 mg/kg) produced convulsions (latency, 4.6±0.4 minutes) and death in all vehicle injected mice. ACPC (400 mg/kg) was most efficacious in protecting mice against NMDA-induced convulsions and death when administered 15 minutes prior to NMDA (FIG. 1), with an anticonvulsant effect still manifest after 30 minutes. ACPC protected mice against NMDA-induced convulsions and death in a dose-dependent fashion (100–400 mg/kg) with an ED$_{50}$ of 234 mg/kg (FIG. 2). Both ACPCM (19–114 mg/kg) and ACPCE (39–156 mg/kg) afforded dose-dependent protection against NMDA-induced convulsions and death with ED$_{50}$ values of 46 and 100 mg/kg, respectively (FIG. 2). The anticonvulsant action of ACPCM (114 mg/kg) was manifest more rapidly than ACPC but of shorter duration, with the maximum efficacy apparent 5–15 minutes after injection (FIG. 1). Complete protection against NMDA-induced convulsions was not observed with these 1-aminocyclopropanecarboxylates, and supramaximal doses resulted in statistically significant reductions (p<0.01, X$^2$) in their efficacies. In contrast, complete protection against NMDA-induced lethality was observed thirty minutes following administration of MK-801 (1 mg/kg) (Table 1, legend). A dose of ACPC (400 mg/kg) that was maximally effective against NMDA-induced convulsions and death did not afford significant protection against bicuc., strych. or PTZ-induced convulsions (Table 1). Moreover, the latency to convulsions induced by these agents was not significantly altered by this dose of ACPC (400 mg/kg) (Table 1, legend).

Effect of 1-aminocyclopropanecarboxylates on MES:

Application of 50 mA for 0.2 s through the pinnae produced tonic and clonic seizures in all animals. Neither ACPC (200–2000 mg/kg) nor ACPCM (114–571 mg/kg) had a significant, dose-dependent effect on MES. In contrast, MK-801 (1 mg/kg) administered thirty minutes before MES abolished the hindclimb tonic extensor component in 87% of the mice (Table 1).

Effects of 1-aminocyclopropanecarboxylates on motor performance:

No overt behavioral effects were apparent in mice treated with ACPC (100–2000 mg/kg), ACPCE (39–195 mg/kg), or ACPCM (19–571 mg/kg). Furthermore, no impairment of performance in either the rotarod or hanging wire tests were observed with these doses of ACPC or ACPCM (Table 1). Thirty minutes after administration of MK-801 (1 mg/kg), a profound hyperactivity was apparent accompanied by a complete impairment in both the rotarod and horizontal wire tests (Table 1).

Discussion

ACPC is a potent, competitive inhibitor of strychnine-insensitive [$^3$H]glycine binding to the NMDA receptor complex, and enhances [3H]MK-801 binding to this supramolecular complex with a lower efficacy than glycine (Marvizón et al, 1989). It has been reported that ACPC enhances [$^3$H]TCP binding (Nadler et al, 1988), which provides additional evidence that ACPC compound is capable of modulating NMDA-gated cation channels. It has also been noted that glycine has a relatively high affinity for its modulatory site at the NMDA receptor complex compared with its concentrations in the brain (Johnson and Ascher, 1987). Moreover, the presence of glycine has been shown to be an absolute requirement for activation of NMDA receptors expressed in Xenopus oocytes (Kleckner & Dingledine, 1988).

We have examined the effects of ACPC on chemically- and electrically-induced convulsions sensitive to both competitive and non-competitive NMDA antagonists (Clineschmidt et al, 1982; Croucher et al, 1982; Czuczwar and Meldrum, 1982; Czuczwar et al, 1985; Turski et al, 1987; Leander et al, 1988; Loscher et al, 1988; Rogawski et al, 1988). Both a "bell-shaped" dose-response curve, and an inability of ACPC to completely block NMDA-induced convulsions (maximum protection of =85% was observed at 400 mg/kg) were seen.

Since the effects of a partial agonist at glycine receptors should be most apparent under conditions of excessive NMDA receptor activation (for example, after administration of convulsant doses of NMDA), this may help to explain the apparent selectivity of ACPC as an anticonvulsant compared to both competitive and non-competitive NMDA antagonists (Clineschmidt et al, 1982a; Croucher et al, 1982; Czuczwar and Meldrum, 1982; Czuczwar et al, 1985; Turski et al, 1987; Leander et al, 1988; Loscher et al, 1988; Rogawski et al, 1988). Similarly, the lack of overt behavioral effects or neuro-toxicity seen with ACPC, which indicate it would have a more favorable "therapeutic index" than NMDA antagonists (Clineschmidt et al, 1982b; Bennett and Amrick, 1986; Compton et al, 1987; Rogawski et al, 1988; Loscher et al, 1988), may also be attributable to its partial agonist action, since substitution of glycine with ACPC would reduce, but not completely inhibit activity at NMDA-operation cation channels.

Furthermore, we note that the potency of systemically administered ACPC was also determined (ED$_{50}$ 234 mg/kg), and was found to be lower than would be predicted from its affinity (K$_1$=32 nM) for strychnine-insensitive glycine receptors in vitro (Marvizón et al, 1989). This apparent anomaly may be attributable to its presence as a zwitterion at physiological pH which could impede its penetration through the blood-brain barrier. This hypothesis was tested by examining the actions of the methyl-(APCPM) and ethyl-(ACPCE) esters of ACPC. ACPCM and ACPCE were found to be ~5- and ~2.3-fold more potent, respectively, than their parent compound. These findings indicate that more lipophilic derivatives of ACPC may enter the central nervous system in greater quantities than the parent compound. However, several lines of evidence suggest that both ACPCE and ACPCM must be converted to ACPC in order to elicit an anticonvulsant action. Thus, despite their higher potencies in vivo, both the methyl and ethyl esters are more than three orders of magnitude less potent than ACPC as inhibitors of [$^3$H]glycine binding in vitro (Table 1). Moreover, like the parent compound, both ACPCE and ACPCM exhibited a "bell-shaped" dose response curve, and neither ester could completely block NMDA-induced convulsions and deaths, and no overt behavioral effects or neurotoxicity were observed (Table 1).

These findings suggest that the strychnine-insensitive glycine binding site represents a target for the design of agents capable of selectively modulating NMDA-operated ion channels. Thus, ACPC and related compounds may be useful (Lehmann et al, 1987; Robinson and Coyle, 1987) in the treatment of neuropathological conditions associated with excessive activation at NMDA coupled cation channels.

TABLE I

| Compound | ACPC | ACPCE | ACPCM | MK-801 |
|---|---|---|---|---|
| Effect on convulsions induced by: | | | | |
| MDA (125) | +(100–500) | +(39–195) | +(19–190) | +(1)[3] |
| PTZ (80) | –(400) | ND | ND | +[2] |
| STRYCH. (2) | –(400) | ND | ND | –[2] |
| BICUC. (6) | –(400) | ND | ND | +[2] |
| MES | –(200–2000) | ND | –(114–571) | +(1)[1,3] |
| Effect on motor activity: % Impairment | | | | |
| Rotarod | 0 (400–2000) | ND | 0 (114–571) | 100 (1) |
| Hanging Wire | 0 (400–2000) | ND | 0 (114–571) | 100 (1) |
| Inhibition of [$^3$H] glycine binding | | | | |
| IC$_{50}$ (nm) | 38 ± 7[4] | >40,000 | >40,000 | noncompetitive[3] |

Table I Legend:

Pharmacological properties of 1-aminocyclopropanecarboxylates: comparison with MK-801. Values in parentheses are the dose range(s) in mg/kg. All drugs were administered intraperitoneally and evaluated as described in Methods. Symbols: +, active; –, inactive; ND, not determined. The doses of strychnine, pentylenetetrazole and bicuculline used induced convulsions in 100% of the mice with latencies of 3.1±0.4, 1.4±0.2, and 2.1±0.3 min., respectively. At least 10 mice/group were used to evaluate the anticonvulsant and behavioral profiles at each dose of 1-aminocyclopropanecarboxylates. MK-801 (1 mg/kg) was included as a positive control since the anticonvulsant and psychopharmacological profile of this non-competitive NMDA antagonist has been characterized.

Superscripts refer to: [2]Clineschmidt et al, 1982a; [1]Leander et al, 1988; [3]Marvizon and Skolnick, 1988; and 4Marvizon et al, 1989. Marvizon and Skolnick, 1988 have demonstrated that MK-801 (10 μM) non-competitively inhibits activation of [$^3$H]glycine binding by $Mg^{+2}$.

Pharmaceutical Compositions

The Formula I partial agonist compounds of the present invention may be made into sterile pharmaceutical compositions for injection, by combination with appropriate pharmaceutically acceptable carriers or diluents, and may be formulated into preparations in liquid for injections in the usual ways for this respective route of administration. The following methods and excipients are merely exemplary and are in no way to be construed as limiting.

In pharmaceutical dosage forms, the compounds of the present invention may be used in the form of their pharmaceutically acceptable salts, and also may be used alone or in appropriate association, as well as in combination with other pharmaceutically active compounds.

The compounds of the present invention may be formulated into preparations for injections by dissolving, suspending or emulsifying them in an aqueous or non-aqueous solvent, such as vegetable oil, synthetic aliphatic acid glycerideds, esters of higher aliphatic acids or propylene glycol; and if desired, with conventional additives such as solubilizers, isotonic agents, suspending agents, emulsifying agents, stabilizers and preservatives.

The amount of the compounds of the present invention to be used may vary according to the severity and type of neuropsychopharmacological disorder, as well as the amount of excess NMDA receptor activation encountered. Nonetheless, a suitable dosage is thought to be about 2 to 10 mg/kg body weight, and of course, the preferred dosage is that amount sufficient to render controllable the neuropsychopharmacologic disorder encountered.

Parenteral administration of the compounds of the present invention can easily be had by a pharmaceutically acceptable carrier, such as Sterile Water for Injection, USP, or by a sterile saline solution.

The Formula I partial agonists provided herein, may be formulated into unit dosage forms, wherein the term "unit dosage forms" refers to physically discrete units suitable as unitary dosages for human as well as animal subjects, each unit containing a predetermined quantity of a Formula I partial agonist compound calculated in an amount sufficient with a pharmaceutically acceptable, diluent, carrier or vehicle. The specifications for the novel unit dosage forms of the present invention depend on the particular compound employed and the effect to be achieved, and the pharmacodynamics associated with each compound in the host.

The pharmaceutically acceptable adjuvants, for example, vehicles, carrier of diluents are readily available to the public. The amount of one of the neuropsychopharmacological treating partial agonists' compounds disclosed herein can be determined by the particular neuropsychopharmacological disorder treating activity of each compound per se.

Possible routes of administration include intravenous (i.v.), subcutaneous (s.c.), intramuscular (i.m.) and intraperitoneal (i.p.).

Any necessary adjustments in dose can be readily made to meet the severity of the neuropsychopharmacological disorder encountered and adjusted accordingly by the skilled practitioner.

Lastly, the scope of the present invention is to be considered as limited only by the scope of claims appended hereto.

References

1. Anderson, P., Christy, M., and Edwards, B.; Dibenzo cyclohepteniminies, U.K. Patent (GB 2 004 873 B), 1982.
2. Aprison, M., and Daly, E.: Biochemical aspects of transmission at inhibitory synapses: the role of glycine. Adv. Neurochem. $\underline{3}$: 203–294, 1978.
3. Bennett, D. and Amrick, C.: 2-Amino-7-phosphoheptanoic acid (AP7) proiduces discriminative stimuli and anticonflict effects similar to diazepam. Life Sci. $\underline{39}$: 2455–2461.
4. Bristow, D., Bowery, N., and Woodruff, G.: Light microscopic autoradiographic localization of [$^3$H] glycine and [$^3$H]strychnine binding sites in a rat brain. Europ. J. Pharmacol. $\underline{126}$: 303–307, 1986.
5. Clineschmidt, B., Martin, G., and Bunting, P.: Anticonvulsant activity of (+)-5-Methyl-10,11-dihydro-5H-dibenzo[a,d]cyclohepten-5,10-imine (MK-801), a substance with potent anticonvulsant, central sympathomimetic, and apparent anxiolytic properties. Drug. Dev. Res. $\underline{2}$: 123–134, 1982a.
6. Clineschmidt, B., Williams, M., Witoslawski, J., Bunting, P., Risley, A., and Totaro, J.: Restoration of shock-suppressed behavior by treatment with (+)-5-Methyl-10,11-dihydro-5H-dibenzo[a,d]cyclohepten-5,10-imine (MK-801), a substance with potent anticonvulsant, central sympathomimetic, and apparent anxiolytic properties. Drug Dev. Res. $\underline{2}$: 147–163, 1982b.
7. Compton, R., Contreras, P., O'Donohue, T. and Monahan, J.: The N-methyl-D-aspartate antagonist, 2-amino-7-phosphonoheptanoate, produces phencyclidine-like behavioral effects in rats. Eur. J. Pharmacol. $\underline{136}$: 133–134, 1987.
8. Czuczwar, S. and Meldrum, B.: Protection against chemically induced seizures by 2-amino-7-phosphonoheptanoic acid. Eur. J. Pharmacol. $\underline{83}$: 335–338, 1982.
9. Czuczwar, S., Frey, H., and Loscher, W.: Antagonism of N-methyl-D, L-aspartic acid-induced convulsions by antiepileptic and other agents. Eur. J. Pharmacol. $\underline{108}$: 273–280, 1985.
10. Dunham, N. and Miya, T., 1956: A note on a simple apparatus for detecting neurologic deficit in rats and mice. J. Amerc. Pharm. Assoc. $\underline{3}$: 112–113.
11. Foster, A., and Fagg, G.: Taking apart NMDA receptors. Nature $\underline{329}$: 395–396, 1987.
12. Galli A., Fenigli, S., Anichini, A., and Pizzighelli, L.: Stereoselective inhibition of [$^3$H]glycine binding to cortical membranes of rat brain by amino acids. Pharmacol. Res. Comm. $\underline{20}$: 407–408, 1988.
13. Hunkeler, W., Mohler, H., Pieri, L., Polc, P., Bonetti, E., Cumin, R., Schaffner, R., and Haefely, W.: Selective antagonists of benzodiazepines. Nature $\underline{290}$: 513–516, 1981.
14. Johnson, J. W., and Ascher, P.: Glycine potentiates the NMDA response in cultured mouse brains neurons. Nature $\underline{25}$: 529–531, 1987.
15. Kleckner, N. W. and Dingledine, R., 1988: Requirement for glycine in activation of NMDA-receptors expressed in Xenopus oocytes. Science $\underline{241}$: 835–837, 1988.
16. Lamanec, T., Bender, D., DeMarco, M., Karady, S., Reamer, R., Weinstock, L.: α-effect nucleophiles: a novel and convenient method for the synthesis of dibenzo[a,d]cycloheptenimines. J. Org. Chem. $\underline{53}$: 1768–1774, 1988.
17. Leander, J., Rathbun, R., and Zimmerman, D.: Anticonvulsant effects of phencyclidine-like drugs: relation to N-methyl-D-aspartate antagonism. Brain Res. $\underline{454}$: 358–372, 1988.
18. Lehmann, J., Schneider, J. and Williams, M.: Excitatory amino acids and mammalian CNS function. Ann. Rep. Med. Chem. $\underline{22}$: 31–40, 1987.

19. Loscher, W., Nolting, B., and Honack, D.: Evaluation of CPP, a selective NMDA antagonist, in various rodent models of epilepsy. Comparison with other NMDA antagonists, in various rodent models of epilepsy. Comparison with other NMDA antagonists, and with diazepam and phenobarbital. Eur. J. Pharmacol. 152: 9–17, 1988.

20. Marvizón, J., Vázquez, J., Garcia Calvo, M., Mayor, F., Jr., Ruiz Gómez, A., Valdivieso, F., and Benavides, J.: The glycine receptor: pharmacological studies and mathematical modeling of the allosteric interaction between the glycine and the strychnine binding sites. Mol. Pharmacol. 30: 590–597, 1988.

21. Marvizón, J., and Skolnick, P.: [$^3$H]Glycine binding is modulated by $Mg^{2+}$ and other ligands of the NMDA receptor-cation channel complex. European J. Pharmacol. 151: 157–158, 1988.

22. Marvizón, J., Lewin, A., and Skolnick, P.: 1-Aminocyclopropanecarboxylic acid: a potent and selective ligand for the glycine modulatory site of the N-Methyl-D-Aspartate receptor complex. J. Neurochem., 52: 52:992–994, 1989.

23. Marwaha, J., Palmer, M., Hoffer, B., Freedman, R., Rice, K., Paul, S., and Skolnick, P.: Differential electrophysiological and behavioral responses to optically active derivatives of phencyclidine. Naunyn-Schmiedeberg's Arch. Pharmacol. 315: 203–209, 1981.

24. Nadler, V., Kloog, Y. and Sokolovsky, M.: 1-Aminocyclopropane-1-carboxylic acid (ACC) mimics the effects of glycine on the NMDA receptor ion channel. Eur. J. Pharmacol. 157: 115–116, 1988.

25. Ransom, R. and Stec, N.: Cooperative modulation of [$^3$H]MK-801 binding to the N-methyl-D-Aspartate receptor-ion channel complex by L-glutamate, glycine and polyamines. J. Neurochem. 51: 830–836, 1988.

26. Reynolds, I., Murphy, S., and Miller, R.: $^3$H-labeled MK-801 binding to the excitatory amino acid receptor complex from rat brain is enhanced by glycine. Proc. Natl. Acad. Sci. (USA) 84: 7744–7748, 1987.

27. Robinson, M. B. and J. T. Coyle: Glutamate and related excitatory amino neurotransmitters: from basic science to clinical application. FASEB J. 1: 446–455, 1987.

28. Rogawski, M., Thurkauf, A., Rice, K., Jacobsen, A., and Mullen, J.: Anticonvulsant activity of phencyclidine analogs: structural modifications resulting in enhanced seizure protection relative to motor side effects. In: Frontiers in excitatory amino acid research. Ed. by E. Cavalheireo, J. Lehmann, and L. Turski, pp. 227–230, A. R. Liss, Inc., New York, 1988.

What is claimed is:

1. A method of treating a neuropsychopharmacological disorder in a patient, wherein the neuropsychopharmacological disorder treated results from or is associated with excessive activation of the N-methyl-D-aspartate receptor complex, the method comprising:
   administering to a patient in need of treatment thereof a composition consisting of a compound possessing partial agonist properties for the strychnine insensitive glycine modulatory site of the N-methyl-D-aspartate receptor complex when compared with the endogenous neurotrnasmitter glycine in an amount effective to alleviate the symptoms of the neuropsychopharmacological disorder.

2. The method of claim 1, wherein the neuropsychopharmacological disorder treated is selected from: epilepsy, stroke, anxiety, Alzheimer's disease, Parkinson's Disease, Guam ALS, dementia, and lathyrism.

3. The method of claim 1, wherein the neuropsychopharmacological disorder is an epilepsy or anxiety disorder.

4. The method of claim 1, wherein the disorder is an epilepsy disorder.

5. A method of treating a neuropsychopharmacological disorder in a patient, wherein the neuropsychopharmacological disorder treated results from or is associated with excessive activation of the N-methyl-D-aspartate receptor complex, the method comprising administering an effective amount of a compound having the formula:

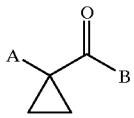

Formula I, wherein
   A is —$NH_2$, —$NHR^1$ or —$NR^1R^2$;
   B is —OH or —$OR^3$;
   $R^1$, $R^2$ and $R^3$, same or different, are selected from lower alkyl, which may be substituted by halogen, hydroxyl, lower alkoxy, oxo, mercapto, aryl or amino; or a pharmaceutically acceptable salt thereof.

6. The method of claim 5, wherein the neuropsychopharmacological disorder is an epilepsy, stroke or anxiety disorder.

7. The method of claim 5, wherein the neuropsychopharmacological disorder is an epilepsy or anxiety disorder.

8. The method of claim 5, wherein the neuropsychopharmacological disorder is an epilepsy disorder.

9. The method of claim 1, wherein the neuropsychopharmacological disorder is an epilepsy or an anxiety disorder, and the compound has the formula:

Formula Ia

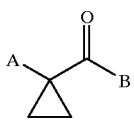

wherein
   $A^1$ is —$NH_2$, —$NHR^1$ or —$NR^1R^2$;
   $B^1$ is —OH or —$OR^3$;
   $R^1$, $R^2$ and $R^3$, same or different, are lower alkyl; or a pharmaceutically acceptable salt thereof.

10. The method of claim 9, wherein A is —$NH_2$.

11. The method of claim 9, wherein A is $NH_2$ and B is —$OR_3$.

12. The method of claim 1, wherein the compound utilized to treat the disorder is selected from the group consisting of
   1-aminocyclopropanecarboxylic acid,
   1-aminocyclopropanecarboxylic acid methyl ester,
   1-aminocyclopropanecarboxylic acid ethyl ester; and
pharmaceutically acceptable salts thereof.

13. The method of claim 1, wherein the neuropsychopharmacological disorder is an epilepsy or anxiety disorder, and the compound utilized to treat the disorder is selected from the group consisting of
   1-aminocyclopropanecarboxylic acid,
   1-aminocyclopropanecarboxylic acid methyl ester, 1-aminocyclopropanecarboxylic acid ethyl ester; and pharmaceutically acceptable salts thereof.

14. The method of claim 1, wherein the neuropsychopharmacological disorder is epilepsy, and the compound utilized to treat the disorder is selected from the group consisting of 1-aminocyclopropanecarboxylic acid, 1-aminocyclopropanecarboxylic acid methyl ester, 1-aminocyclopropanecarboxylic acid ethyl ester; and pharmaceutically acceptable salts thereof.

15. A pharmaceutical composition for the treatment of a neuropsychopharmacological disorder which results from or is associated with excessive activation of the N-methyl-D-aspartate receptor complex, comprising:

(a) a compound having the formula:

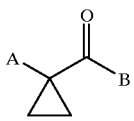

Formula I wherein

A is $-NH_2$, $-NHR^1$ or $-NR^1R^2$;

B is $-OH$ or $-OR^3$;

$R^1$, $R^2$ and $R^3$, same or different, are selected from lower alkyl, which may be substituted by halogen, hydroxyl, alkoxy, oxo, mercapto, aryl or amino; or a pharmaceutically acceptable salt thereof; and (b) a pharmaceutically acceptable carrier thereof suitable for administration to a patient, wherein when the carrier is water, the carrier further includes isotonic agents.

16. The pharmaceutical composition of claim 15, wherein the composition comprises an amount of compound in a dosage unit form effective to treat the symptoms of an epilepsy or anxiety disorder.

17. The pharmaceutical composition of claim 15, wherein the composition comprises an amount of compound in a dosage unit from effective to treat the symptoms of an epilepsy disorder.

18. The pharmaceutical composition of claim 16, wherein A is $-NH_2$.

19. The pharmaceutical composition of claim 16, wherein A is $NH_2$ and $R^3$ is lower alkyl.

20. The composition of claim 15, wherein the compound is selected from the group consisting of 1-aminocyclopropanecarboxylic acid, 1-aminocyclopropanecarboxylic acid methyl ester, 1-aminocyclopropanecarboxylic acid ethyl ester; or a pharmaceutically acceptable salt thereof.

21. The composition of claim 15, wherein the carrier is suitable for intravenous administration.

* * * * *